(12) United States Patent
Weekes et al.

(10) Patent No.: US 10,092,301 B2
(45) Date of Patent: Oct. 9, 2018

(54) ORTHOPAEDIC REAMER CONNECTOR

(71) Applicant: Symmetry Medical Manufacturing, Inc., Warsaw, IN (US)

(72) Inventors: Stuart Weekes, Oxford (GB); James Truscott, Swindon (GB); Guillaume Kerboul, Crudwell (GB)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 0 days.

(21) Appl. No.: 15/648,642

(22) Filed: Jul. 13, 2017

(65) Prior Publication Data

US 2017/0303936 A1    Oct. 26, 2017

Related U.S. Application Data

(63) Continuation-in-part of application No. 14/547,887, filed on Nov. 19, 2014.

(51) Int. Cl.
| | |
|---|---|
| *A61B 17/16* | (2006.01) |
| *A61B 17/17* | (2006.01) |
| *F16D 1/02* | (2006.01) |
| *A61B 17/00* | (2006.01) |

(52) U.S. Cl.
CPC ...... *A61B 17/1617* (2013.01); *A61B 17/1613* (2013.01); *A61B 17/1622* (2013.01); *A61B 17/1666* (2013.01); *A61B 17/1675* (2013.01); *A61B 17/1684* (2013.01); *A61B 17/1735* (2013.01); *F16D 1/02* (2013.01); *A61B 17/1778* (2016.11); *A61B 2017/00464* (2013.01); *A61B 2017/00477* (2013.01)

(58) Field of Classification Search
CPC .................. A61B 17/1666; A61B 17/162
See application file for complete search history.

(56) References Cited

U.S. PATENT DOCUMENTS

| | | | |
|---|---|---|---|
| 5,658,290 | A | 8/1997 | Lechot |
| 6,854,742 | B2 | 2/2005 | Salyer et al. |
| 7,115,119 | B2 | 10/2006 | Desarzens |
| 8,323,284 | B2 | 12/2012 | Ferreira |
| 8,366,713 | B2 | 2/2013 | Long et al. |

(Continued)

FOREIGN PATENT DOCUMENTS

| | | |
|---|---|---|
| WO | 03/094739 A2 | 11/2003 |
| WO | 2010/004267 A1 | 1/2010 |

OTHER PUBLICATIONS

Extended European Search Report dated Apr. 21, 2016 for European Patent Application No. 15 19 1155 (6 pages).

*Primary Examiner* — Andrew Yang
(74) *Attorney, Agent, or Firm* — Taylor IP, P.C.

(57) ABSTRACT

An orthopedic reamer connector includes a holder section shaped to allow for connection of an orthopedic reamer, the holder section including a connection surface and two pairs of holders associated with the connection surface, each of the two pairs of holders having a first holder and a second holder that forms an acute angle relative to the first holder, the first holders being opposed to each other by about 180 degrees and the second holders being opposed to each other by about 180 degrees; and a stop section mechanically interlocked with the holder section so as to prevent relative rotation therebetween and including a pair of stops associated with each of the two pairs of holders, each of the pair of stops having a first stop associated with the first holder and a second stop associated with the second holder.

20 Claims, 5 Drawing Sheets

(56) References Cited

U.S. PATENT DOCUMENTS

| | | |
|---|---|---|
| 8,398,642 B2 | 3/2013 | Weekes |
| 8,439,920 B2 | 5/2013 | Ryall et al. |
| 2003/0216716 A1 | 11/2003 | Desarzens |
| 2012/0023733 A1 | 2/2012 | Cannell et al. |
| 2013/0213678 A1 | 8/2013 | Weekes |
| 2013/0253520 A1 | 9/2013 | Ryall et al. |

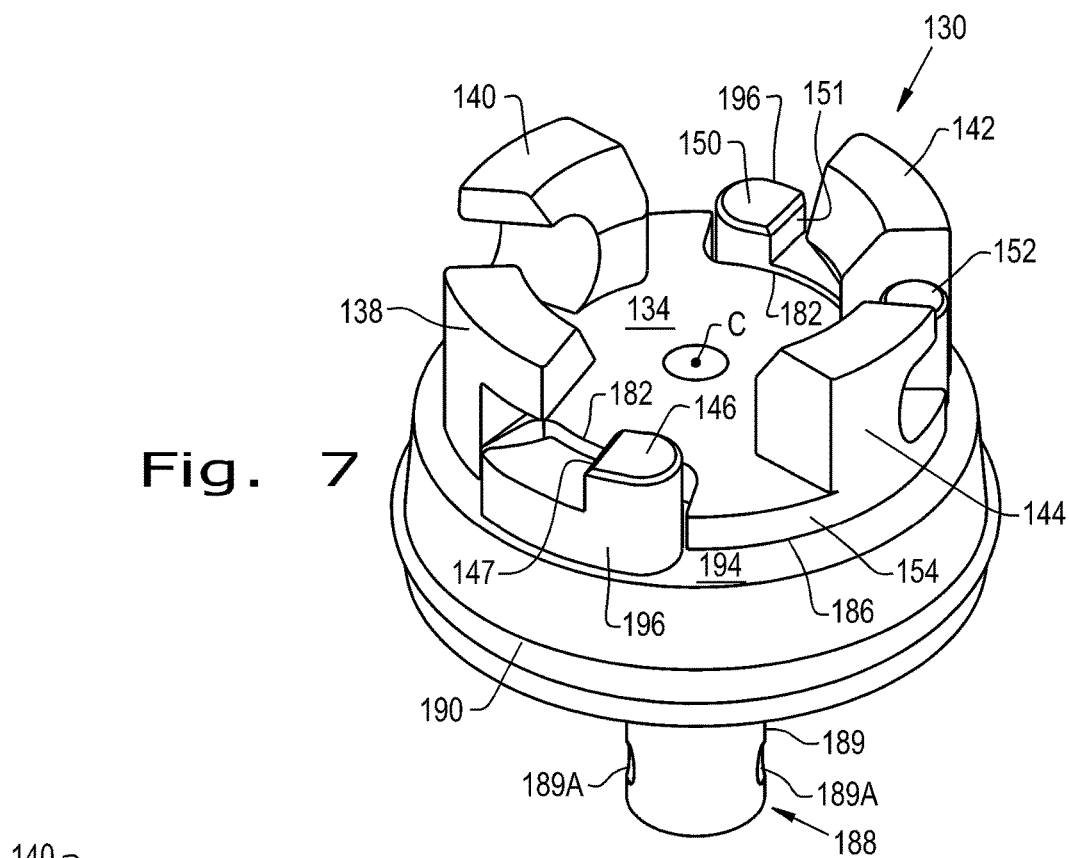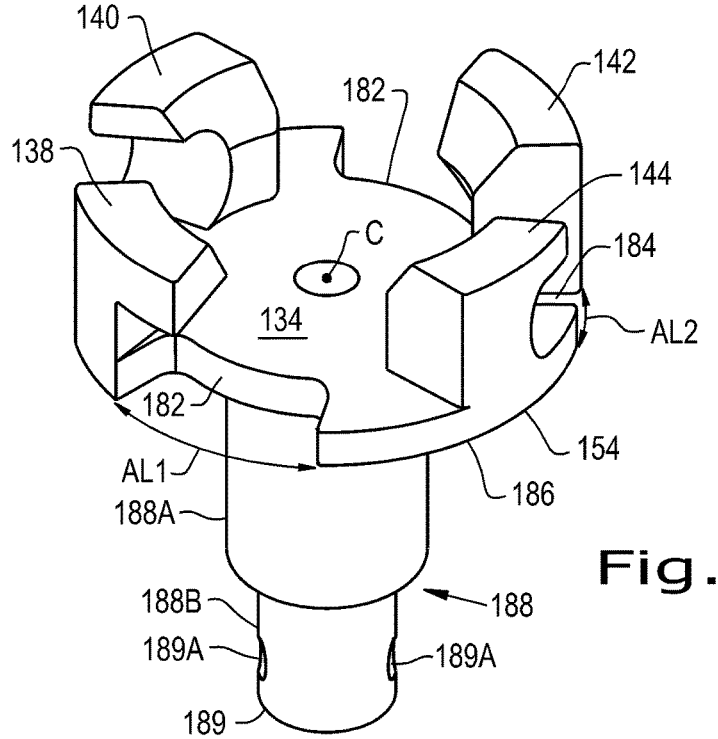

ORTHOPAEDIC REAMER CONNECTOR

CROSS REFERENCE TO RELATED APPLICATIONS

This is a continuation-in-part of U.S. patent application Ser. No. 14/547,887, entitled "ORTHOPAEDIC REAMER CONNECTOR", filed Nov. 19, 2014, which is incorporated herein by reference.

BACKGROUND OF THE INVENTION

1. Field of the Invention

The present invention relates to connectors, and, more particularly, to orthopaedic reamer connectors.

2. Description of the Related Art

In the field of orthopaedic surgery, it is often necessary to remove bone material to enable implantation of a prosthesis to repair joints in the human body. Patella cutters and acetabular reamer cups and glenoid reamers are surgical tools which are used in surgery for the insertion of artificial joints. Acetabular reamer cups are used to cut hemispherical cavities in pelvis bones for the insertion of artificial hip joints. Patella cutters are used to shape the underside of the patella or knee cap during knee replacement surgery. Glenoid reamers are used to cut hemispherical cavities in shoulder bones for the insertion of artificial shoulder joints. Patella cutters have a complex arrangement of precisely shaped cutting edges arranged around an axis of rotation for cutting the patella. Acetabular reamer cups and glenoid reamers have a complex arrangement of cutting edges arranged on a spherical surface around the axis of rotation of the cup.

A number of tools have been developed for this purpose and include reamers having generally semi-hemispherical configuration with cutting elements on them so that a corresponding semi-hemispherical hollow can be formed in the bone material for providing a foundation for the repair of the joint.

There are two major driver styles in the field, one of which is for the Othy style manufactured by Symmetry Medical, Inc. and the other style manufactured by Precimed SA of L'Echelette, Switzerland (now owned by Greatbatch Medical). Although these both have semi-hemispherical cutting heads, they have different interfaces between driving tools with which they are associated. The Othy style has a crossbridge (also known as a bridgeback) element. This element is a bar extending between the circumference of the hemisphere and having a circular expanded section in the middle. Numerous arrangements are available for securing this device as exemplified by U.S. Pat. No. 6,854,742. Alternatively, the Precimed reamer has a crossbar shape in which two circular cross section bars intersect at the center and extend to the walls of the hemisphere and is known as a cruciform reamer. An example of a driver for this type is found in U.S. Pat. No. 5,658,290 in which a bayonet interconnection is provided between the reamer and the driver.

Typically, surgeons use specialized drivers for each of the reamers. The drivers connect to a source of power and have appropriate handles for guiding the operation of the reamer by a surgeon. If a surgeon has one of the adaptors, it is difficult to utilize the other type of reamer since it requires a specialized driver for that reamer. It has been proposed in U.S. Pat. No. 7,115,119 to provide a dual adapter that accommodates both the Othy and the Precimed reamers. This type of driver has a bayonet interconnection in which the assemblies are inserted axially and then a rotational movement, in accordance with a bayonet connection, is provided to lock the elements in place. The bayonet connection of the driver has a two-tiered construction, which requires a more complicated manufacturing process.

One additional consideration when designing orthopaedic reamer connectors is the ability to sterilize the reamer connector after contacting biological tissues and fluids; if the reamer connector cannot be sterilized between uses, the reamer connector must be single-use. Single-use reamer connectors, generally, are not economically feasible for users due to the high cost associated with creating the complex connector shapes and the materials required to provide the necessary strength. Further, many reamer connectors are formed as one-piece items which must be entirely replaced when the reamer connector becomes inoperable due to, for example, wear.

What is needed in the art is an orthopaedic reamer connector that can accommodate multiple styles of reamers, be sterilized between uses and be more economically replaced or repaired compared to known reamer connectors.

SUMMARY OF THE INVENTION

The present invention provides an orthopaedic reamer connector with a holder section having two pairs of holders that are opposed to each other by 180 degrees, the holders of each pair forming an acute angle therebetween, and a stop section mechanically interlocked with the holder section and having a stop associated with each holder.

The invention in one form is directed to an orthopaedic reamer connector including: a holder section shaped to allow for connection of an orthopaedic reamer, the holder section including a connection surface and two pairs of holders associated with the connection surface, each of the two pairs of holders having a first holder and a second holder that forms an acute angle relative to the first holder, the first holders being opposed to each other by about 180 degrees and the second holders being opposed to each other by about 180 degrees; and a stop section mechanically interlocked with the holder section so as to prevent relative rotation therebetween and including a pair of stops associated with each of the two pairs of holders, each of the pair of stops having a first stop associated with the first holder and a second stop associated with the second holder.

The invention in another form is directed to an orthopaedic reamer including a handle and an orthopaedic reamer connector connected to the handle. The orthopaedic reamer connector includes a holder section shaped to allow for connection of an orthopaedic reamer, the holder section including a connection surface and two pairs of holders associated with the connection surface, each of the two pairs of holders having a first holder and a second holder that forms an acute angle relative to the first holder, the first holders being opposed to each other by about 180 degrees and the second holders being opposed to each other by about 180 degrees; and a stop section mechanically interlocked with the holder section so as to prevent relative rotation therebetween and including a pair of stops associated with each of the two pairs of holders, each of the pair of stops having a first stop associated with the first holder and a second stop associated with the second holder.

An advantage of the present invention is that it can connect to both a bridgeback style reamer and a cruciform style reamer.

Another advantage is that the holder section can be separated from the stop section to sterilize the sections and, when necessary, replace one of the sections without having to replace the entire reamer connector.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 7 is a perspective view of an alternative embodiment of an orthopaedic reamer connector formed according to the present invention;

FIG. 8 is a perspective view of a holder section of the orthopaedic reamer connector shown in FIG. 7;

Corresponding reference characters indicate corresponding parts throughout the several views. The exemplification set out herein illustrates one embodiment of the invention and such exemplification is not to be construed as limiting the scope of the invention in any manner.

DETAILED DESCRIPTION OF THE INVENTION

Figure 1:
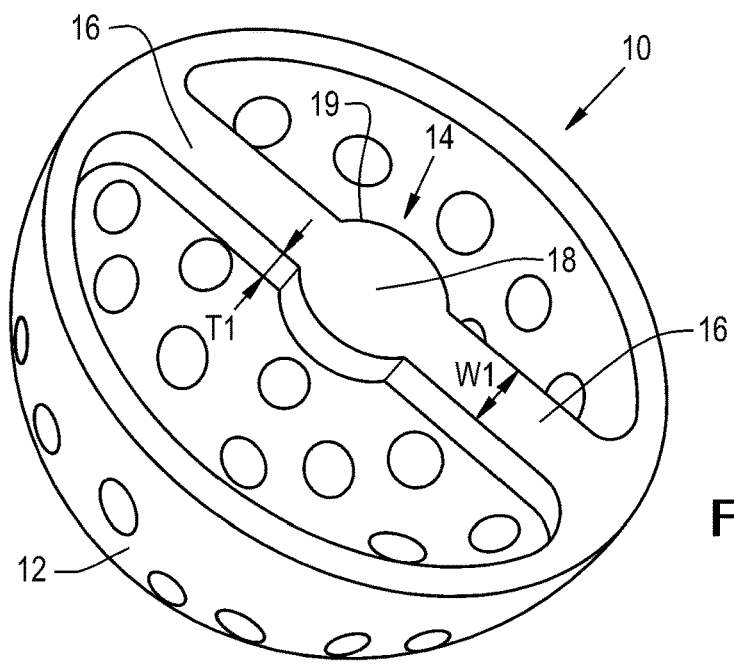
FIG. 1 is a perspective view of a prior art orthopaedic reamer that utilizes the bridgeback connection style.

Referring now to the drawings, and more particularly to FIG. 1, there is shown a bridgeback reamer 10, which can also be referred to as an Othy style reamer, which generally includes a reamer surface 12 and a connecting portion 14 attached to the reamer surface 12. As can be seen, the reamer surface 12 has a semi-spherical shape with the connecting portion 14 extending across a diameter D1 of the bottom of the reamer 10. The connecting portion 14 includes two bridge portions 16 which have a substantially rectangular cross-section that meet at a central hub 18 which has a circular shape. The connecting portion 14 of reamer 10 connects to an orthopaedic reamer driver (not shown) through an orthopaedic reamer connector (such as the one shown in FIGS. 3-6) and drive train (not shown). The drive train allows for the orthopaedic reamer connector to be rotated by a rotary actuator, such as a medical power drill, and that rotation is transferred to the reamer 10 by the orthopaedic reamer connector.

Figure 2:
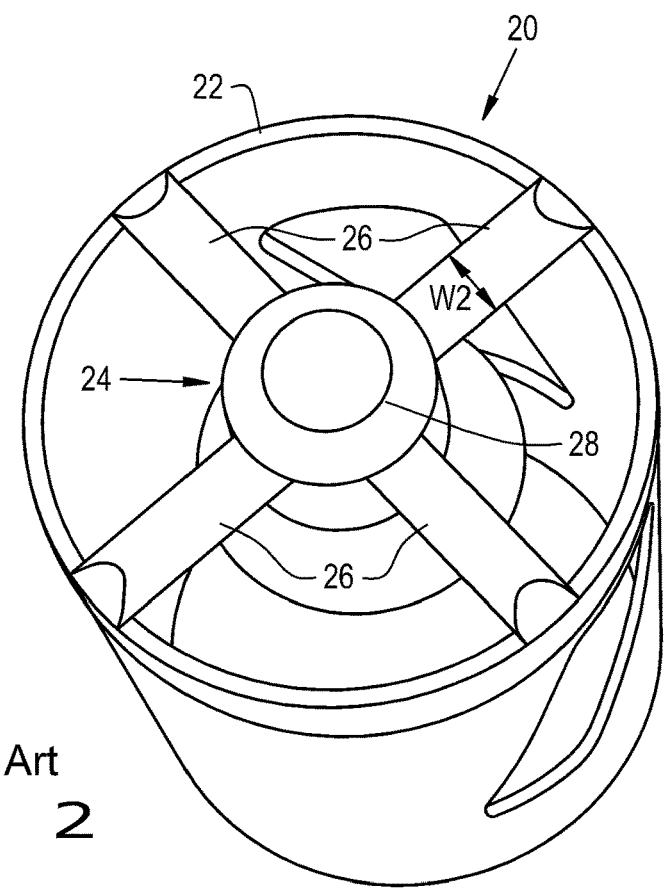
FIG. 2 is a perspective view of a prior art orthopaedic reamer that utilizes the cruciform connection style.

Referring now to FIG. 2, a cruciform reamer 20, which can also be referred to as a Precimed style reamer, is shown. As can be seen, the cruciform reamer 20 has a circular bottom 22 that has a connecting portion 24 for connecting to an orthopaedic reamer connector. The connecting portion 24 includes four spokes 26 that meet at a central hub 28 which has a circular shape. The spokes 26 extend from the bottom 22 to the central hub 28 and each spoke 26 forms a generally 90 degree angle to adjacent spokes 26. Similarly to the bridgeback reamer 10 shown in FIG. 1, the cruciform reamer 20 can be connected to an orthopaedic reamer connector to be driven by a rotary actuator.

As can be seen from FIGS. 1 and 2, the bridgeback reamer 10 and cruciform reamer 20 have significantly different connecting portions 14, 24. As the reamers 10, 20 are modular, it is desirable that an orthopaedic reamer connector is able to connect to and drive both reamer styles.

Figure 3:
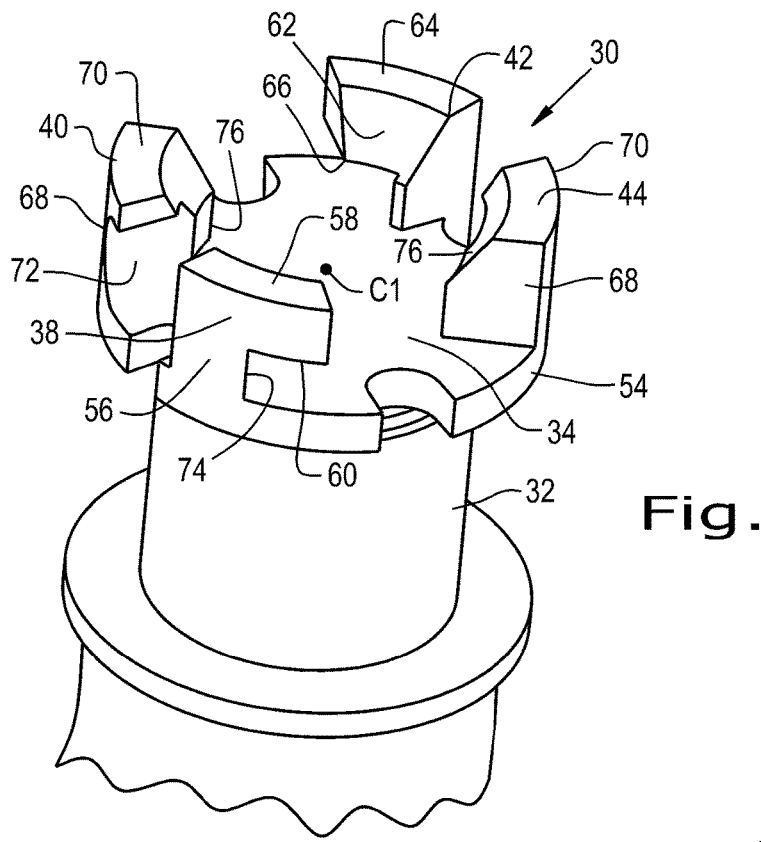
FIG. 3 is a perspective view of an embodiment of an orthopaedic reamer connector according to the present invention.

Referring now to FIG. 3, an embodiment of an orthopaedic reamer connector 30 according to the present invention is shown which generally includes a base 32 with a connection surface 34, two pairs of holders 38, 40, 42, 44 associated with the connection surface 34, and a pair of stops 46, 48, 50, 52 associated with each pair of holders 38, 40, 42, 44. The base 32 has a drive train connector (not shown) held within the orthopaedic reamer connector 30 that rotatably attaches to a drive train (not shown) which is attached to a rotary actuator, such as a medical power drill, so that the torque generated by the rotary actuator can be transferred to the base 32 and rotate an attached orthopaedic reamer. Any type of drive train connector that can allow for the base 32 to be rotated by the rotary actuator can be used, and many types of such connections are known. The base 32 can have a roughly annular cross-section, as shown, with a center C1, which will also be the center of rotation of the base 32, and a circumference 54 defined about center C1, but other shapes can be chosen. The base 32 should be sufficiently sized to allow for connecting portions, such as connecting portions 14 and 24 shown in FIGS. 1 and 2, to be held by the orthopaedic reamer connector 30 during use. Since the orthopaedic reamer connector 30 is likely to encounter bodily fluids and tissues during use, it is useful if the base 32, and other components of the orthopaedic reamer connector 30, are formed from biocompatible materials that do not present local toxicity during use of the orthopaedic reamer. Such materials can include, but are not limited to, cobalt chrome, stainless steel, titanium, tantalum, ultra-high molecular weight polyethylene (UHMWPE), and poly ether etherketone (PEEK). The base 32 can be formed by any fabrication capable of producing a suitable shape, such as casting, machining, molding, punching, extrusion, etc.

The orthopaedic reamer connector 30 has two pairs of holders 38, 40, 42 and 44 associated with the connection surface 34. As used herein when describing the holders 38, 40, 42 and 44, "associated with" can mean, among other things, "formed on," "connected to," "held by," "held with," and "attached to," such that the holders 38, 40, 42 and 44 can act as holding structural features in conjunction with the connection surface 34. The holders 38, 40, 42 and 44 are arranged in pairs, with holders 38 and 40 forming a pair and holders 42 and 44 forming a pair. In this regard, holders 38 and 42 can each be considered first holders of their respective pair and holders 40 and 44 can each be considered second holders of their respective pair. As can be seen, holders 38, 40, 42 and 44 all extend at least partially away from the base 32 and connection surface 34 so that when the base 32 and holders 38, 40, 42 and 44 rotate, an object that radially extends, relative to center C1, to or past the holders 38, 40, 42 and 44 and is abutting the connection surface 34 will be forced against one or more of the holders 38, 40, 42 and 44 and rotate along with the base 32. The first holders 38 and 42 are opposed about 180 degrees relative to each other and the second holders 40 and 44 are also opposed about 180 degrees relative to each other. As used herein, "opposed about 180 degrees relative to each other" signifies that the first holders 38 and 42 and second holders 40 and 44 are held at opposed locations relative to the center C1, i.e., a straight line can be drawn through first holders 38 and 42 that passes through center C1 and a straight line can be drawn through second holders 40 and 44 that passes through center C1. The first holders 38, 42 and their respective second holders 40, 44 also form an acute angle relative to each other. The significance of the acute angle between the first holders 38 and 42 and their respective second holders 40 and 44 will be described below. Such an arrangement is in contrast to other known orthopaedic reamer connectors, where the holders are arranged so that a 90 degree angle is formed between adjacent holders on the connection surface.

Figure 4:
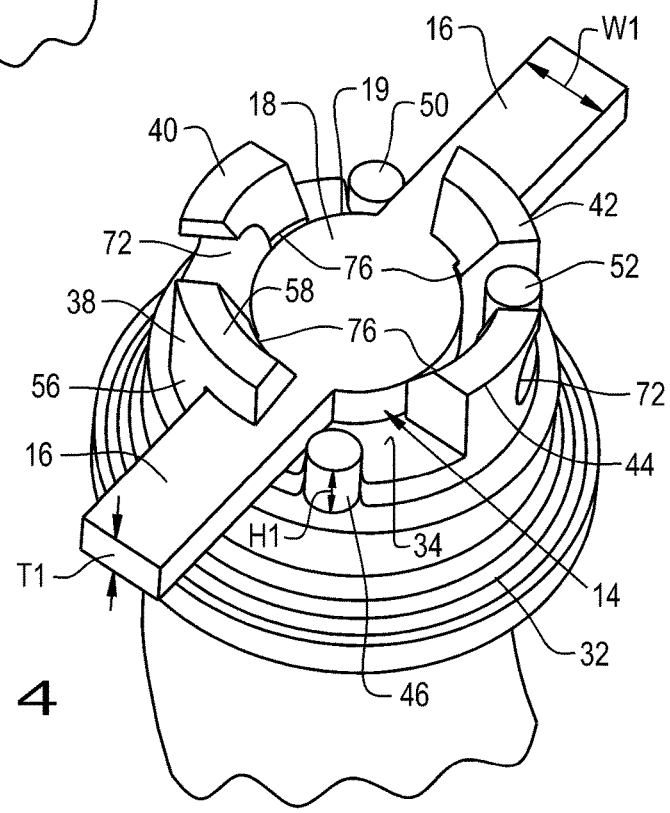
FIG. 4 is a perspective view of the orthopaedic reamer connector shown in FIG. 3 connected to a bridgeback orthopaedic reamer.
Figure 5:
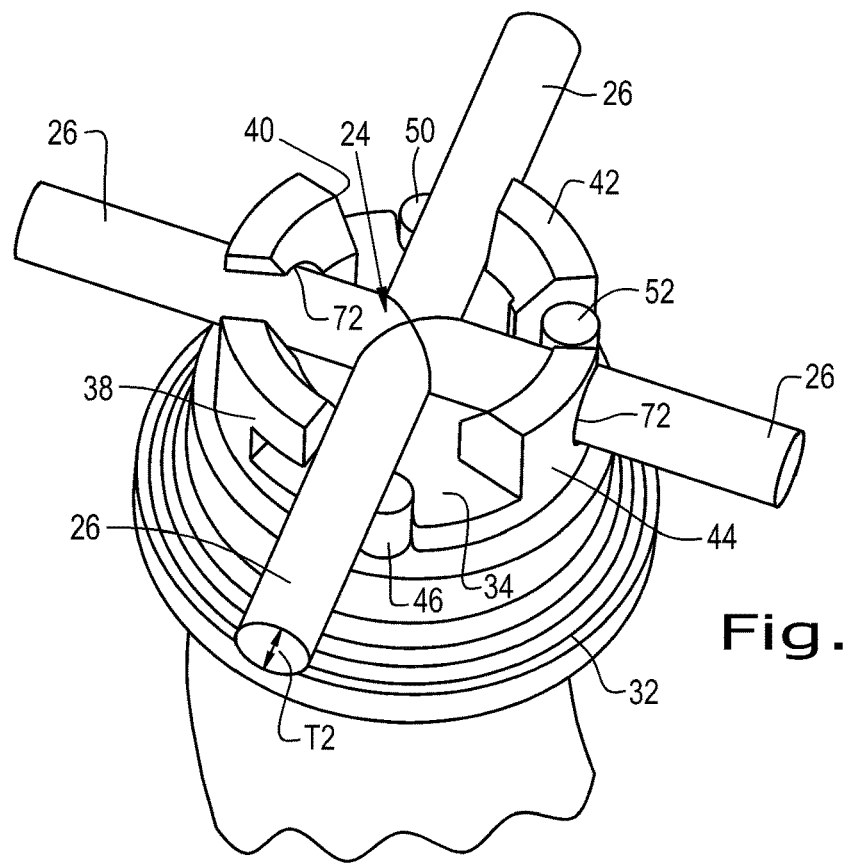
FIG. 5 is a perspective view of the orthopaedic reamer connector shown in FIGS. 3-4 connected to a cruciform orthopaedic reamer.

As can be seen, the holders 38, 40, 42 and 44 can have different shapes. As shown, first holder 38 can be formed as an L-shaped hook with a vertical portion 56 that extends away from the connection surface 34 and a horizontal portion 58 that extends along the circumference 54 of the connection surface 34. Such a shape forms a holding channel 60 between a part of the horizontal portion 58 and the connection surface 34 that faces associated stop 46, where part of an orthopaedic reamer connecting portion can be held during use. The length of the vertical portion 56 and horizontal portion 58 can be adjusted, as desired, to accommodate various sizes and shapes of orthopaedic reamer connecting portions. First holder 42, as shown, has a wedge shape with a curved surface 62 that extends radially outward from a point on the base 32 to an annular surface 64 that extends along circumference 54. A channel 66 can be formed between the holder 42 and connecting surface 34 that faces associated stop 50, as shown in FIGS. 4 and 5. Optionally, first holder 42 could be formed as a mirror image of first holder 38, i.e., an L-shaped hook. Second holders 40 and 44 can have vertical portions 68 and horizontal portions 70 similar to first holder 38, while also having rounded edges 72 formed in the second holders 40 and 44 that face associated stops 48 and 52. The rounded edges 72 can be sized to accommodate a cruciform reamer, such as reamer 20 shown in FIG. 2, so that the spokes 26 of the reamer 20 will be held against the rounded edges 72, as shown in FIG. 5. In this regard, first holders 38 and 42 can be sized and shaped to engage a bridgeback reamer 10 during rotation of the base 32 and second holders 40 and 44 can be sized and shaped to engage a cruciform reamer 20 during rotation of the base 32. It should be appreciated that the described and shown shapes of the holders 38, 40, 42 and 44 are exemplary only and can be modified in different ways without straying from the spirit of the present invention.

Figure 6:
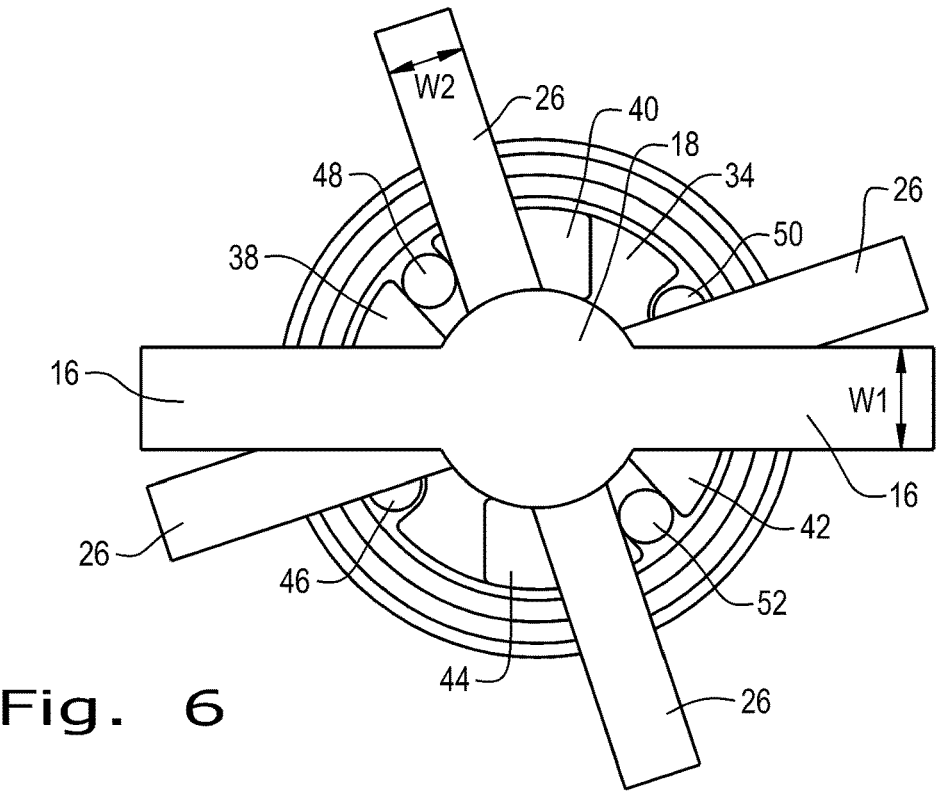
FIG. 6 is a top view of the orthopaedic reamer connector shown in FIGS. 3-5 overlayed with both a bridgeback and cruciform orthopaedic reamer.

As can be seen in FIGS. 4-6, the orthopaedic reamer connector 30 also includes two pairs of stops 46, 48, 50 and 52 associated with the holders 38, 40, 42 and 44. As used herein when describing the stops 46, 48, 50 and 52, "associated with" signifies that each stop 46, 48, 50 and 52 has an associated holder 38, 40, 42 and 44, respectively, that the stop is distanced from so that both the stop and its associated holder can act in concert to contact opposing surfaces of an object placed in between and cause the object to rotate along with the orthopaedic reamer connector 30. In this regard, stops 46 and 50 can be considered first stops since stop 46 is associated with first holder 38 and stop 50 is associated with first holder 42 and stops 48 and 52 can be considered second stops since stop 48 is associated with second holder 40 and stop 52 is associated with second holder 44. Similar to the first holders 38, 42 and second holders 40, 44, the first stops 46 and 50 can form an acute angle relative to their paired second stops 48 and 52, respectively. As the first stops 46 and 50 are associated with the first holders 38 and 42, the first stops 46 and 50 can be held a distance from their associated first holders 38 and 42 that corresponds to a width W1 of the bridge portions 16 of the bridgeback reamer 10. Such a distancing allows for the bridgeback reamer 10 to be tightly held against the first holders 38 and 42 and first stops 46 and 50 to secure the bridgeback reamer 10 to the orthopaedic reamer connector 30, as can be seen in FIG. 4. As can be seen, the vertical portion 56 of first holder 38 has an abutting surface 74 that the bridgeback reamer 10 connecting portion 14 can abut against when connected to the orthopaedic reamer connector 30. The distance between the abutting surface 74 and first stop 46 can therefore be close to the width W1 of the bridge portions 16 so that opposite edges of one of the bridge portions 16 will contact both the abutting surface 74 and first stop 46 during use and movement of the bridge portions 16 along the circumference 54 can be minimized. In a similar fashion, first stop 50 can have a distance from contacting surface 66 of first holder 42 that corresponds to the width W1 of the bridge portions. Similarly, second stops 48 and 52 can be held a distance from their associated second holders 40 and 44 that corresponds to a width W2 of the spokes 26 of the cruciform reamer 20. Such a distancing allows for the cruciform reamer 20 to be tightly held against the second holders 40 and 44 and first stops 48 and 52 to secure the cruciform reamer 20 to the orthopaedic reamer connector 30, as can be seen in FIG. 5.

The stops 46, 48, 50 and 52 can all be similarly shaped or have different shapes, as desired. As shown in FIGS. 4-6, the stops 46, 48, 50 and 52 are configured as pins that are spring loaded so they can be pushed down below the connecting surface 34 to allow for connecting portions 14, 24 to be placed against their respective holders 38, 40, 42 and 44 and then naturally push back up to hold the connecting portions 14, 24 between the stops 46, 48, 50 and 52 and their associated holders 38, 40, 42 and 44.

Referring now to FIG. 4, the connecting portion 14 of the bridgeback reamer 10 is shown connected to the orthopaedic reamer connector 30. As can be seen, the bridge portions 16 extend radially past the circumference 54 of the connection surface 34 and abut against first holders 38 and 42 and first stops 46 and 50. The vertical portion 56 of holder 38 extends a distance from the connection surface 34 that is close to a thickness T1 of the bridge portions 16, to constrain movement of the connecting portion 14 in a direction away from the connection surface 34. In this regard, the bridge portions 16 being held between the channel 60 and first stop 46 and the channel 66 and first stop 50 constraints rotation of the connecting portion 14 relative to the orthopaedic reamer connector 30 and movement of the connecting portion 14 away from the connection surface 34. Optionally, the holders 38, 40, 42 and 44 can all have curved portions 76 that abut against a circumference 19 of the central hub 18 when the connecting portion 14 is placed against the connection surface 34, further securing the connecting portion 14 to the orthopaedic reamer connector 30.

Since the connecting portion 14 of the bridgeback reamer 10 only has two bridge portions 16, second holders 40 and 44 and second stops 48 and 52 do not contact the bridge portions 16 when the bridgeback reamer 10 is connected to the orthopaedic reamer connector 30. To assist a user with determining which of the holders 38, 40, 42 and 44 and stops 46, 48, 50 and 52 correspond to the connecting portion 14 of the bridgeback reamer 10, the first stops 46 and 50 can be shorter than second stops 48 and 52, due to the thickness T1 of the connecting portion 14 of the bridgeback reamer 10 generally being less than a thickness T2 of the connecting portion 24 of the cruciform reamer 20. Since the thickness T1 is less than the thickness T2, the first stops 46 and 50 can have a smaller height H1 to constrain the connecting portion 14 of the bridgeback reamer 10 than the second stops 48 and 52 which can have a larger height H2 to constrain the connecting portion 24 of the cruciform reamer 20. If the thickness T1 of the bridgeback reamer 10 is greater than the thickness T2 of the cruciform reamer 20, the height H1 of first stops 46 and 50 can be greater than the height H2 of second stops 48 and 52.

Referring now to FIG. 5, the orthopaedic reamer connector 30 is shown connected to the connecting portion 24 of the cruciform reamer 20. As can be seen, two spokes 26 of the connecting portion 24 are held between the rounded edges 72 of second holders 40 and 44 and their associated stops 48 and 52 and the other two spokes abut against the holders 38 and 42. The stops 48 and 52 have a greater height H2 than stops 46 and 50, as previously described, to correspond to the thickness T2 of the cruciform reamer 20. Since the stops 46, 48, 50 and 52 can be spring loaded pins, the spokes 26 can be pressed down toward the connection surface 34 to push down the stops 46, 48, 50 and 52 then rotated to place two of the spokes 26 between the rounded edges 72 of second holders 40 and 44 and their associated stops 48 and 52. Since stops 46 and 50 are pressed down by spokes 26 and spring loaded, stops 46 and 50 will provide an upward force against the spokes 26 to better secure the cruciform reamer 20 to the orthopaedic reamer connector 30.

FIG. 6 shows an overlay of how the bridgeback reamer 10 and cruciform reamer 20 will both look when connected to the orthopaedic reamer connector 30 of the present invention. As can be seen, the bridge portions 16 of the bridgeback reamer 10 are significantly wider than the spokes 26 of the cruciform reamer 20. This width difference makes it difficult to accommodate both reamers 10, 20 using an orthopaedic reamer connector that has four equally spaced holders that form 90 degree angles relative to each other. By utilizing two opposed pairs of holders 38, 40, 42 and 44 with a first holder 38, 42 and a second holder 40, 44 that form an acute angle relative to each other in combination with associated first stops 46, 50 and second stops 48, 52, both the bridgeback reamer 10 and cruciform reamer 20 can be secured to the orthopaedic reamer connector 30 without using a two-tiered construction. Further, since the first holders 38, 42 and first stops 46, 50 primarily hold the bridgeback reamer 10 and the second holders 40, 44 and second stops 48, 52 primarily hold the cruciform reamer 20, the holders 38, 40, 42, 44 and stops 46, 48, 50, 52 can be more specifically tailored to the connecting portions 14, 24 of the reamers 10 and 20. As such, the holders 38, 40, 42 and 44 and stops 46, 48, 50, and 52 can be adjusted to accommodate many different types of modular reamers.

Referring now to FIGS. 7-10, an alternative embodiment of an orthopaedic reamer connector 130 formed according to the present invention is shown. As the orthopaedic reamer connector 130 is similar to the previously described orthopaedic reamer connector 30, similar elements of orthopaedic reamer connector 130 are assigned similar reference numerals raised by 100. The orthopaedic reamer connector 130 includes a holder section 180 shaped to allow for connection of an orthopaedic reamer, such as previously described bridgeback reamer 10 and cruciform reamer 20, and a stop section 190 mechanically interlocked with the holder section 180 so as to prevent relative rotation between the holder section 180 and the stop section 190. The holder section 180, which is shown by itself in FIG. 8, includes a pair of first holders 138, 142 and a pair of second holders 140, 144, which can be similar to the holders 38, 40, 42, 44 of the orthopaedic reamer connector 30, and has a connection surface 134. The connection surface 134 can be formed as a substantially round shape, similar to connection surface 34, with a center C and a peripheral surface 154, shown as a circumference. One or more cutouts 182, 184 can be formed in the peripheral surface 154 between the holders 138, 140, 142, 144, the significance of which will be described further herein. The holder section 180 can also have a base bottom surface 186 opposite the connection surface 134 and a driving stem 188 connected to the base bottom surface 186. The driving stem 188 can be shaped to connect to a drive train (not shown) at a driving end 189 of the driving stem 188. The driving stem 188 can be formed as a pair of connected cylindrical sections 188A, 188B, with the first cylindrical section 188A being connected to the base bottom surface 186 and having a greater diameter than the second cylindrical section 188B which defines the driving end 189 and has a pair of openings 189A for connecting to a drive train. When connected to a drive train, the driving stem 188 can cause the holder section 180 to be rotated by, for example, a rotary actuator and drive the connected orthopaedic reamer connector. The cutouts 182, which can be referred to as a pair of first cutouts, can be placed on opposite sides of the center C so that the first cutouts 182 are separated from one another by 180 degrees about the center C. Similarly, the cutouts 184, which can be referred to as a pair of second cutouts, can be placed on opposite sides of the center C so that the second cutouts 184 are separated from one another by 180 degrees about the center C. The first cutouts 182 can be formed to have a first arc length AL1 which is greater than a second arc length AL2 of the second cutouts 184, the significance of which will be further described herein.

Figure 9:
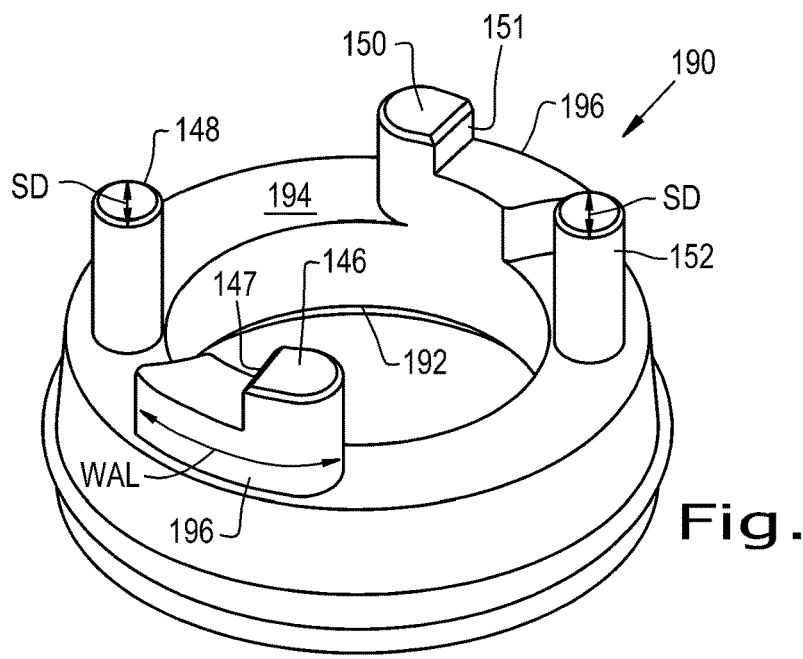
FIG. 9 is a perspective view of a stop section of the orthopaedic reamer connector shown in FIG. 7.
Figure 10:
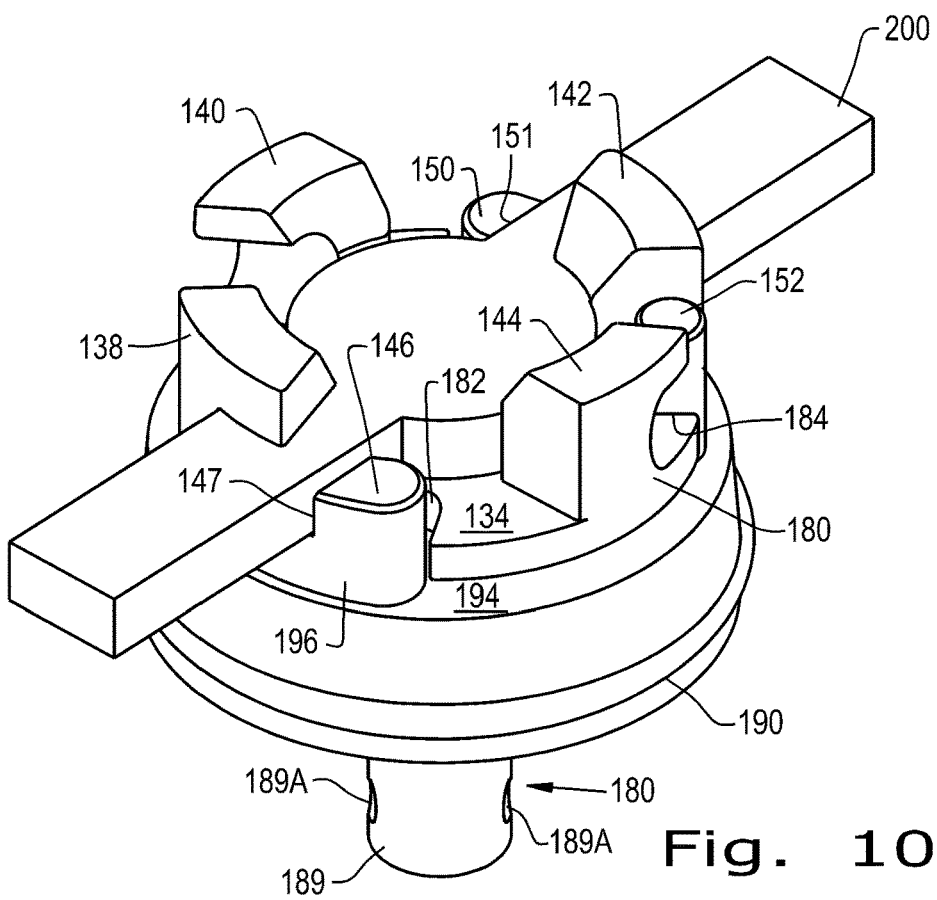
FIG. 10 is a perspective view of the orthopaedic reamer connector shown in FIG. 7 connected to a bridgeback orthopaedic reamer.

The stop section 190, which is shown by itself in FIG. 9, includes stops 146, 148, 150, 152 which are associated with the holders 138, 140, 142, 144 of the holder section 180, similar to the previously described orthopaedic reamer connector 30. The stops 146 and 150, for example, are a pair of first stops 146, 150 each associated with a respective one of the first holders 138, 142 and the stops 148, 152 are a pair of second stops 148, 152 each associated with a respective one of the second stops 148, 152. As shown, the stop section 190 can be formed as a circular collar having a circular opening 192 through which the driving stem 188 is placed so portions of the base bottom surface 186 of the holder section 180 abut against a top surface 194 of the stop section 190, as can be seen in FIG. 7. To reduce toggle prior to use of the orthopaedic reamer connector 130, the top surface 194 of the stop section 190 can be substantially flat, i.e., planar, so the base bottom surface 186 can sit flush on the top surface 194. The holders 138, 140, 142, 144 in conjunction with the stops 146, 148, 150, 152 of the orthopaedic reamer connector 130 can accommodate various types of orthopaedic reamer connections, such as a bridgeback connection 200 shown in FIG. 10, similarly to the previously described orthopaedic reamer connector 30.

To mechanically interlock the stop section 190 to the holder section 180 so as to prevent relative rotation therebetween when, for example, the driving stem 188 is rotatably driven, the pair of first stops 146, 150 can each be formed on raised wedges 196 of the stop section 190. As can be seen, each of the first stops 146, 150 can be formed to have a partially arcuate shape including a respective straight edge 147, 151 which will abut against the connected orthopaedic reamer connection 200. Alternatively, the first stops 146, 150 can be completely round, similar to the second stops 148, 152. The raised wedges 196 can each define a wedge arc length WAL that closely matches the first arc length AL1 of the first cutouts 182 so the raised wedges 196 can be placed within the first cutouts 182 and substantially fill the first cutouts 182 to abut against the material of the holder section 180. Similarly, the pair of second stops 148, 152 can each define a stop diameter SD that closely matches the second arc length AL2 of the second cutouts 184 so the second stops 148, 152 can be placed within the second cutouts 184 and substantially fill the second cutouts 184 to abut against the material of the holder section 180. By having the stops 146, 148, 150, 152 placed within the cutouts 182, 184 and abutting against material of the holder section 180, the stop section 190 mechanically interlocks to the holder section 180 such that rotation of the holder section 180 will also cause rotation of the stop section 190, allowing the holder section 180 and stop section 190 to, in conjunction, rotate a connected orthopaedic reamer. Optionally, the wedge arc lengths WAL and stop diameters SD of the stops 146, 148, 150, 152 can be smaller than the corresponding first arc lengths AL1 and second arc lengths AL2 to allow for some movement of the second stops 148, 152 and raised wedges 196 within their respective cutouts 182, 184 in order to accommodate connection to differently sized reamer connections, i.e., the second stops 148, 152 and raised wedges 196 can be forced into abutting contact with the material of the holder section 180 upon being connected to the reamer and/or during rotation. Further, the mechanical interlocking between the holder section 180 and stop section 190 can be reversed by disconnecting the driving stem 188 of the holder section 180 from a drive train and pulling the holder section 180 apart from the stop section 190, allowing the holder section 180 and stop section 190 to be sterilized separately.

In one exemplary embodiment of the present invention, the holder section 180 and the stop section 190 can be formed of different materials. For example, the holder section 180 can be formed of a relatively high strength material, such as stainless steel, while the stop section 190 is formed of a lower strength material, such as polytetrafluoroethylene (PTFE), so that the stop section 190 is more prone to wear during rotation of the orthopaedic reamer connector 130 than the holder section 180. It should be appreciated that the previously described materials are exemplary only, and other types of materials can be utilized to form the holder section 180 and stop section 190. As the holder section 180 has a relatively complex shape compared to the stop section 190 and can experience large stresses at the driving stem 188, forming the holder section 180 from a higher strength material than the stop section 190 allows the holder section 180 to be re-usable for many uses of the orthopaedic reamer connector 130. The stop section 190, on the other hand, can be formed in a relatively cost-efficient manner by, for example, molding and can therefore be a single-use item or relatively inexpensive to replace due to wear. It should therefore be appreciated that the present invention provides an orthopaedic reamer connector 130 which can accommodate different types of reamer connections, be easily sterilized, and have a section that is relatively economical to replace.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic reamer connector, comprising:
a holder section shaped to allow for connection of an orthopaedic reamer, said holder section including a connection surface and two pairs of holders associated with said connection surface, each of said two pairs of holders having a first holder and a second holder that forms an acute angle relative to said first holder, said first holders being opposed to each other by about 180 degrees and said second holders being opposed to each other by about 180 degrees, said holder section defining a longitudinal axis through the connection surface; and
a stop section mechanically interlocked with said holder section so as to prevent relative rotation therebetween and including a pair of stops associated with each of said two pairs of holders, each of said pair of stops having a first stop associated with said first holder and a second stop associated with said second holder, wherein each of said first stops forms an acute angle with its paired second stop relative to the longitudinal axis.

2. The orthopaedic reamer connector according to claim 1, wherein said first holders are first hooks and said second holders are second hooks.

3. The orthopaedic reamer connector according to claim 2, wherein said first hooks are configured to engage a bridgeback reamer and said second hooks are configured to engage a cruciform reamer.

4. The orthopaedic reamer connector according to claim 3, wherein said holder section includes a base bottom surface opposite said connection surface and a driving stem connected to said base bottom surface and configured to rotatably connect to a rotary actuator.

5. The orthopaedic reamer connector according to claim 4, wherein said stop section is a collar with a collar opening formed therein, said driving stem being at least partially held within said collar opening.

6. The orthopaedic reamer connector according to claim 1, wherein said holder section includes a peripheral surface and at least one cutout formed in said peripheral surface and said stop section includes at least one raised wedge including at least one of said first stop and said second stop formed thereon, said at least one raised wedge being placed within said at least one cutout so as to abut against said holder section and prevent relative rotation between said stop section and said holder section.

7. The orthopaedic reamer connector according to claim 6, wherein said at least one cutout includes a first pair of cutouts and said at least one raised wedge includes a first pair of raised wedges, each of said first pair of raised wedges being placed in a respective one of said first pair of cutouts and including one of said first stops.

8. The orthopaedic reamer connector according to claim 6, wherein said at least one raised wedge substantially fills said at least one cutout.

9. The orthopaedic reamer connector according to claim 6, wherein said at least one cutout includes a plurality of cutouts and said at least one raised wedge includes a plurality of raised wedges.

10. The orthopaedic reamer connector according to claim 6, wherein said at least one cutout includes a second pair of cutouts and each of said second stops is placed within a respective one of said second pair of cutouts.

11. An orthopaedic reamer, comprising:
a handle; and
an orthopaedic reamer connector connected to said handle, said orthopaedic reamer connector including:
a holder section shaped to allow for connection of an orthopaedic reamer, said holder section including a connection surface and two pairs of holders associated with said connection surface, each of said two pairs of holders having a first holder and a second holder that forms an acute angle relative to said first holder, said first holders being opposed to each other by about 180 degrees and said second holders being opposed to each other by about 180 degrees, said holder section defining a longitudinal axis through the connection surface; and
a stop section mechanically interlocked with said holder section so as to prevent relative rotation therebetween and including a pair of stops associated with each of said two pairs of holders, each of said pair of stops having a first stop associated with said first holder and a second stop associated with said second holder, wherein each of said first stops forms an acute angle with its paired second stop relative to the longitudinal axis.

12. The orthopaedic reamer according to claim 11, wherein said first holders are first hooks and said second holders are second hooks.

13. The orthopaedic reamer according to claim 12, wherein said first hooks are configured to engage a bridge-back reamer and said second hooks are configured to engage a cruciform reamer.

14. The orthopaedic reamer according to claim 13, wherein said holder section includes a base bottom surface opposite said connection surface and a driving stem connected to said base bottom surface and configured to rotatably connect to a rotary actuator.

15. The orthopaedic reamer according to claim 14, wherein said stop section is a collar with a collar opening formed therein, said driving stem being at least partially held within said collar opening.

16. The orthopaedic reamer according to claim 11, wherein said holder section includes a peripheral surface and at least one cutout formed in said peripheral surface and said stop section includes at least one raised wedge including at least one of said first stop and said second stop formed thereon, said at least one raised wedge being placed within said at least one cutout so as to abut against said holder section and prevent relative rotation between said stop section and said holder section.

17. The orthopaedic reamer according to claim 16, wherein said at least one cutout includes a first pair of cutouts and a second pair of cutouts and said at least one raised wedge includes a first pair of raised wedges and a second pair of raised wedges, each of said first pair of raised wedges being placed in a respective one of said first pair of cutouts and including one of said first stops and each of said second pair of raised wedges being placed in a respective one of said second pair of cutouts and including one of said second stops.

18. The orthopaedic reamer according to claim 16, wherein said at least one raised wedge substantially fills said at least one cutout.

19. The orthopaedic reamer according to claim 16, wherein said at least one cutout includes a plurality of cutouts and said at least one raised wedge includes a plurality of raised wedges.

20. The orthopaedic reamer according to claim 16, wherein said at least one cutout includes a second pair of cutouts and each of said second stops is placed within a respective one of said second pair of cutouts.

* * * * *